(12) United States Patent
Suma et al.

(10) Patent No.: US 11,364,185 B2
(45) Date of Patent: Jun. 21, 2022

(54) ZINC OXIDE POWDER, DISPERSION, AND COSMETICS

(71) Applicant: SUMITOMO OSAKA CEMENT CO., LTD., Tokyo (JP)

(72) Inventors: Syunsuke Suma, Tokyo (JP); Shingo Hosoda, Tokyo (JP); Kenichiro Nishida, Tokyo (JP)

(73) Assignee: SUMITOMO OSAKA CEMENT CO., LTD., Tokyo (JP)

(*) Notice: Subject to any disclaimer, the term of this patent is extended or adjusted under 35 U.S.C. 154(b) by 0 days.

(21) Appl. No.: 16/309,388

(22) PCT Filed: Dec. 27, 2016

(86) PCT No.: PCT/JP2016/088878
§ 371 (c)(1),
(2) Date: Dec. 12, 2018

(87) PCT Pub. No.: WO2017/216989
PCT Pub. Date: Dec. 21, 2017

(65) Prior Publication Data
US 2019/0314254 A1 Oct. 17, 2019

(30) Foreign Application Priority Data

Jun. 14, 2016 (JP) .............................. JP2016-118020

(51) Int. Cl.
| | | |
|---|---|---|
| *A61K 8/27* | (2006.01) | |
| *A61K 8/02* | (2006.01) | |
| *A61K 8/04* | (2006.01) | |
| *A61K 8/25* | (2006.01) | |
| *A61K 8/26* | (2006.01) | |
| *A61K 8/44* | (2006.01) | |
| *A61K 8/58* | (2006.01) | |
| *A61K 8/81* | (2006.01) | |
| *A61K 8/92* | (2006.01) | |
| *A61Q 1/02* | (2006.01) | |
| *A61Q 1/12* | (2006.01) | |
| *A61Q 17/04* | (2006.01) | |

(52) U.S. Cl.
CPC ............... *A61K 8/27* (2013.01); *A61K 8/022* (2013.01); *A61K 8/04* (2013.01); *A61K 8/25* (2013.01); *A61K 8/26* (2013.01); *A61K 8/44* (2013.01); *A61K 8/585* (2013.01); *A61K 8/8105* (2013.01); *A61K 8/92* (2013.01); *A61Q 1/02* (2013.01); *A61Q 1/12* (2013.01); *A61Q 17/04* (2013.01); *A61K 2800/262* (2013.01); *A61K 2800/612* (2013.01); *A61K 2800/614* (2013.01)

(58) Field of Classification Search
CPC . A61Q 1/02; A61Q 1/12; A61Q 17/04; A61K 8/27; A61K 8/022; A61K 8/04; A61K 8/25; A61K 8/26; A61K 8/44; A61K 8/585; A61K 8/8105; A61K 8/92; A61K 2800/262; A61K 2800/612; A61K 2800/614
See application file for complete search history.

(56) References Cited

U.S. PATENT DOCUMENTS

| | | | | |
|---|---|---|---|---|
| 7,482,382 | B2* | 1/2009 | Li ........................ | B82Y 30/00 423/594.1 |
| 8,883,312 | B2* | 11/2014 | Yabuki .................. | B82Y 30/00 423/102 |
| 9,855,197 | B2* | 1/2018 | Itagaki .................... | A61K 8/27 |
| 2006/0210495 | A1* | 9/2006 | Meyer ...................... | A61K 8/28 424/59 |
| 2011/0130273 | A1* | 6/2011 | Karpov .................... | C01G 9/02 502/343 |
| 2011/0152433 | A1* | 6/2011 | Bechtloff ................. | A61K 8/27 524/460 |
| 2016/0334720 | A1* | 11/2016 | Ishida ................... | G03G 5/1476 |

FOREIGN PATENT DOCUMENTS

| | | | | |
|---|---|---|---|---|
| JP | 57-205319 | A | 12/1982 | |
| JP | 60-255620 | A | 12/1985 | |
| JP | 63-288913 | A | 11/1988 | |
| JP | 63-288914 | A | 11/1988 | |
| JP | 02-289506 | A | 11/1990 | |
| JP | 03-199121 | A | 8/1991 | |
| JP | 7-118133 | * | 5/1995 | .............. A61K 7/42 |
| JP | 07-118133 | A | 5/1995 | |
| JP | 07-232919 | A | 9/1995 | |
| JP | 2002-201382 | A | 7/2002 | |
| JP | 2007-503373 | A | 2/2007 | |
| JP | 2011-026264 | A | 2/2011 | |
| JP | 2014-201465 | A | 10/2014 | |
| WO | WO-2015072499 | A1* | 5/2015 | .............. A61K 8/25 |

OTHER PUBLICATIONS

Alessio Becheri, et al, Synthesis and Characterization of Zinc Oxide Nanoparticles: Application to Textiles as UV-Absorbers, 10 J Nanopart. Res. 679 (Year: 2008).*
"67. Water-soluble Material Examination Method", The Japanese Standards of Quasi-Drug Ingredients 2006 (JSQI).
International Search Report for PCT/JP2016/088878 (dated Jan. 31, 2017).

* cited by examiner

*Primary Examiner* — Sean M Basquill
(74) *Attorney, Agent, or Firm* — Merchant & Gould P.C.

(57) ABSTRACT

In a zinc oxide powder of the present invention, a content of a water-soluble substance is 0.30% by mass or less, and a mass ratio between an alkali metal and an alkaline earth metal which are included in the water-soluble substance is in a range of 1:2 to 10:1.

20 Claims, No Drawings

ZINC OXIDE POWDER, DISPERSION, AND COSMETICS

TECHNICAL FIELD

The present invention relates to a zinc oxide powder, a dispersion, and a cosmetic.

The present application is a U.S. National Stage Application under 35 U.S.C. § 371 of International Patent Application No. PCT/JP2016/088878 filed on Dec. 27, 2016, which claims the benefit of priority to Japanese Patent Application No. 2016-118020 filed on Jun. 14, 2016, the disclosures of all of which are hereby incorporated by reference in their entireties. The International Application was published in Japanese on Dec. 21, 2017 as WO 2017/216989.

BACKGROUND

A zinc oxide powder has an ultraviolet-shielding function, a gas transmission-suppressing function, and the like and is also highly transparent, and is thus used for applications requiring transparency such as ultraviolet-shielding films, ultraviolet-shielding glass, a cosmetic, and gas barrier films (for example, refer to Patent Literature Nos. 1 to 7).

In addition, it is known that the zinc oxide powder is capable of suppressing the spreading of sebum by solidifying the sebum and thus capable of suppressing make-up fading attributed to sebum by being used in a foundation or the like (for example, refer to Patent Literature No. 8).

However, a certain period of time is required for the zinc oxide powder to solidify sebum, and thus it has been difficult to suppress make-up fading only with the zinc oxide powder.

CITATION LIST

Patent Literature

Patent Literature No. 1: Japanese Laid-open Patent Publication No. 57-205319
Patent Literature No. 2: Japanese Laid-open Patent Publication No. 60-255620
Patent Literature No. 3: Japanese Laid-open Patent Publication No. 63-288913
Patent Literature No. 4: Japanese Laid-open Patent Publication No. 63-288914
Patent Literature No. 5: Japanese Laid-open Patent Publication No. 3-199121
Patent Literature No. 6: Japanese Laid-open Patent Publication No. 7-232919
Patent Literature No. 7: Japanese Laid-open Patent Publication No. 2002-201382
Patent Literature No. 8: Japanese Laid-open Patent Publication No. 2011-26264

SUMMARY OF INVENTION

Technical Problem

The present invention has been made in consideration of the above-described circumstances, and an object of the present invention is to provide zinc oxide powder capable of shortening the time taken for sebum to solidify more than in the related art, a dispersion, and a cosmetic which include the zinc oxide powder.

Solution to Problem

A first aspect of the present invention is a zinc oxide powder in which a content of a water-soluble substance is 0.30% by mass or less, and a mass ratio between an alkali metal and an alkaline earth metal which are included in the water-soluble substance is in a range of 1:2 to 10:1.

In other words, a zinc oxide powder including zinc oxide and a water-soluble substance, in which the content of the water-soluble substance is 0.30% by mass or less, the water-soluble substance include an alkali metal and an alkaline earth metal, and the mass ratio between the alkali metal and the alkaline earth metal which are included in the water-soluble substance is in a range of 1:2 to 10:1 is provided.

The zinc oxide powder of the present invention preferably has the following characteristics. These characteristics may be combined with one another.

A content of zinc oxide in the zinc oxide powder is preferably 99.0% by mass or more.

A specific surface area of the zinc oxide powder is preferably 8 $m^2/g$ or more and 65 $m^2/g$ or less.

The zinc oxide powder is preferably surface-treated with at least one of an inorganic component and an organic component.

The inorganic component is at least one selected from silica and alumina, and the organic component is also preferably at least one selected from the group consisting of a silicone compound, organopolysiloxane, a fatty acid, fatty acid soap, a fatty acid ester, a polyolefin, N-acylamino acid or a salt thereof, N-acyl-N-alkylamino acid or a salt thereof, hydrogenated lecitin or a salt thereof, and an organic titanate compound.

It is preferable that the content of the zinc oxide is 99.0% by mass or more and the content of the water-soluble substance is 0.010% by mass or more and 0.30% by mass or less.

A second aspect of the present invention is a dispersion containing the zinc oxide powder and a dispersion medium.

A third aspect of the present invention is a cosmetic containing the zinc oxide powder and/or the dispersion and a cosmetic base raw material.

Advantageous Effects of Invention

According to the zinc oxide powder of the present invention, the content of the water-soluble substance is 0.30% by mass or less, and the mass ratio between the alkali metal and the alkaline earth metal which are included in the water-soluble substance is in a range of 1:2 to 10:1, and thus it is possible to shorten the time necessary for the solidification of sebum.

According to the dispersion of the present invention, the zinc oxide powder of the present invention and the dispersion medium are included, and thus it is possible to shorten the time necessary for the solidification of sebum.

According to the cosmetic of the present invention, the zinc oxide powder of the present invention and/or the dispersion of the present invention and the cosmetic base raw material are included, and thus it is possible to further suppress make-up fading.

DESCRIPTION OF EMBODIMENTS

Preferred examples of zinc oxide powder, a dispersion, and a cosmetic of the present invention will be described.

Meanwhile, the following examples are simply specific descriptions for the better understanding of the gist of the present invention and do not limit the present invention unless particularly specified. Modification, omission, substitution, addition, and other modification are possible within the scope of the gist of the present invention.

[Zinc Oxide Powder]

The zinc oxide powder of the present invention includes zinc oxide and a water-soluble substance, the content of the water-soluble substance is 0.30% by mass or less, and the mass ratio between the alkali metal and the alkaline earth metal which are included in the water-soluble substance is in a range of 1:2 to 10:1 is provided. Due to these characteristics, it is possible to shorten the time necessary for the solidification of sebum.

The present inventors found that, when the content of the water-soluble substance is set to 0.30% by mass or less, and the mass ratio between the alkali metal and the alkaline earth metal in the water-soluble substance is adjusted to the predetermined range, it is possible to shorten the sebum solidification time and completed the present invention.

(Preferred Content of Water-Soluble Substance)

In the zinc oxide powder of the present invention, the content of the water-soluble substance is 0.30% by mass or less. The content can be arbitrarily selected as long as the content is the above-described value or less; however, for example, more preferably 0.28% by mass or less, still more preferably 0.25% by mass or less, particularly preferably 0.23% by mass or less, and further preferably 0.20% by mass or less. The content is also preferably 0.10% by mass or less.

The water-soluble substance is an impurity derived from a zinc oxide powder. Therefore, a zinc oxide powder that is used in a cosmetic preferably has a small content of the water-soluble substance and more preferably include no water-soluble substance to the possible extent except for the minimum amount of a component capable of accelerating the sebum solidification property. However, realistically, it is difficult to set the content of the water-soluble substance to zero. Therefore, the zinc oxide powder may include a small amount of the water-soluble substance. Therefore, in the zinc oxide powder, the lower limit value of the content of the water-soluble substance may be 0.001% by mass, may be 0.010% by mass, may be 0.050% by mass, may be 0.10% by mass, or may be 0.15% by mass depending on conditions being demanded. Examples of the range of the content of the water-soluble substance with respect to the total amount of the zinc oxide powder include 0.001% by mass to 0.30% by mass, 0.001% by mass to 0.28% by mass, and the like.

When the content of the water-soluble substance exceeds 0.30% by mass, the time necessary for sebum to solidify becomes long. This is because, when the content of the water-soluble substance exceeds 0.30% by mass, the absolute amount of the alkali metal and the alkaline earth metal which are included in the water-soluble substance becomes too large. Therefore, it is assumed that the excessive absolute amount of the alkali metal and the alkaline earth metal impairs the reaction between the zinc oxide powder and a fatty acid and the sebum solidification property becomes poor.

(Alkali Metal in Zinc Oxide Powder)

In the zinc oxide powder of the present invention, the water-soluble substance includes an alkali metal. Only one kind of alkali metal may be included or two or more kinds of alkali metals may be included. In a case in which two or more kinds of alkali metals are included in the water-soluble substance, the total amount of the contents of two or more kinds of the alkali metals is considered as the content of the alkali metal.

In the zinc oxide powder of the present invention, the alkali metal can be exemplified by lithium, sodium, potassium, rubidium, cesium, or francium. The content of the alkali metal is arbitrarily selected, and, for example, is generally 0.001% by mass to 0.75% by mass, preferably 0.001% by mass to 0.2% by mass, and more preferably 0.001% by mass to 0.05% by mass with respect to the total amount of the zinc oxide powder. It is difficult to set the content to 0.001% by mass or less.

(Alkaline Earth Metal in Zinc Oxide Powder)

In the zinc oxide powder of the present invention, the water-soluble substance includes an alkaline earth metal. Only one kind of alkaline earth metal may be included or two or more kinds of alkaline earth metals may be included. In a case in which two or more kinds of alkaline earth metals are included in the water-soluble substance, the total amount of the contents of two or more kinds of the alkaline earth metals is considered as the content of the alkaline earth metal.

In the zinc oxide powder of the present invention, the alkaline earth metal can be exemplified by berylium, magnesium, calcium, strontium, barium, or radium. The content of the alkaline earth metal is arbitrarily selected, and, for example, is generally 0.0001% by mass to 0.2% by mass, preferably 0.001% by mass to 0.1% by mass, and more preferably 0.002% by mass to 0.05% by mass with respect to the total amount of the zinc oxide powder.

(Mass Ratio Between Alkali Metal and Alkaline Earth Metal)

In the water-soluble substance which is included in the zinc oxide powder of the present invention, the mass ratio between the alkali metal and the alkaline earth metal is 1:2 to 10:1. The mass ratio can be selected as necessary within the above-described range and is, for example, preferably 1:2 to 8:1, more preferably 1:2 to 6:1, and still more preferably 1:2 to 3:1. When the mass ratio between the alkali metal and the alkaline earth metal is in the above-described range, it is possible to shorten the time necessary for the solidification of sebum.

(Control of Mass Ratio Between Alkali Metal and Alkaline Earth Metal)

When the mass ratio between the alkali metal and the alkaline earth metal is set to the above-described range, it is possible to shorten the time necessary for the solidification of sebum, but the detail of the mechanism thereof is not clear. However, the mechanism is assumed as described below.

An alkali metal such as sodium or potassium reacts with a fatty acid such as oleic acid which is a sebum component and forms a soluble fatty acid salt. It is assumed that, since the soluble fatty acid salt is likely to dissolve in sweat or moisture and flow, the soluble fatty acid salt hinders the reaction between the zinc oxide powder and the fatty acid on skins, and the sebum solidification property becomes poor. Meanwhile, there is a tendency that, in impurities of the zinc oxide powder, the alkali metal is more included than the alkaline earth metal.

Meanwhile, an alkaline earth metal such as magnesium or calcium reacts with a fatty acid which is included in sebum and forms an insoluble fatty acid salt. The insoluble fatty acid salt does not easily flow into sweat or water. Therefore, the insoluble fatty acid salt does not hinder the reaction between the zinc oxide powder and the fatty acid on skins, and the sebum solidification property is enhanced. An excess increase of impurities is not preferable, and thus it is preferable to control the amount of the alkaline earth metal being included to be appropriate. In the present invention, the amount of the alkaline earth metal is controlled not to become too small.

The amount of an impurity made of an alkali metal or an alkaline earth metal which is included in a zinc oxide powder for cosmetics is small. However, the control of the small content of this impurity in the zinc oxide powder enables the shortening of the time necessary for sebum to solidify.

Regarding the sebum solidification property, it is known that the sebum solidification property preferably has a selectivity of solidifying, among sebum components, a fatty acid which is an oil causing make-up fading (mainly oleic acid) and, on the other hand, not solidifying an emollient component in sebum or an oil included in a cosmetic (Fragrance Journal, December 2015, pp. 42 to 46). Although the reason is not clear, the zinc oxide powder of the present invention has a favorable oleic acid solidification property, but does not solidify cyclopentasiloxane, caprylic/capric triglyceride, squalene, olive oil, and the like which are generally blended into a cosmetic as oils. That is, the zinc oxide powder of the present invention is also capable of obtaining an effect of selectively solidifying a fatty acid (oleic acid).

(Content of Zinc Oxide)

The content of the zinc oxide in the zinc oxide powder of the present invention can be arbitrarily selected. For example, the content is generally 95.0% by mass or more, preferably 98.0% by mass or more, more preferably 99.0% by mass or more, still more preferably 99.1% by mass or more, and particularly preferably 99.2% by mass or more. The content is also preferably 99.4% by mass or more with respect to the total amount of the zinc oxide powder. The upper limit of the content of the zinc oxide in the zinc oxide powder of the present invention can be arbitrarily selected and, for example, may be 100% by mass or less, 99.95% by mass or less, or 99.9% by mass or less, may be 99.8% by mass or less, or may be 99.7% by mass or less. In addition, when the content of the zinc oxide in the zinc oxide powder of the present invention is in the above-described range, it becomes easy to set the content of the water-soluble substance to 0.30% by mass or less by setting the content of the zinc oxide to 99.0% by mass or more and 99.9% by mass or less.

(Specific Surface Area of Zinc Oxide Powder)

The specific surface area of the zinc oxide powder of the present invention can be arbitrarily selected depending on characteristics being demanded. For example, from the viewpoint of transparency, the specific surface area is preferably 8 $m^2/g$ or more and 65 $m^2/g$ or less, more preferably 15 $m^2/g$ or more and 60 $m^2/g$ or less, still more preferably 20 $m^2/g$ or more and 50 $m^2/g$ or less, and most preferably 25 $m^2/g$ or more and 45 $m^2/g$ or less.

When the specific surface area of the zinc oxide powder is in the above-described range, it is possible to enhance the transparency of a dispersion or a cosmetic which contains the zinc oxide powder.

Meanwhile, from the viewpoint of improving the feeling of the zinc oxide powder, the specific surface area is preferably 1 $m^2/g$ or more and 8 $m^2/g$ or less, more preferably 2 $m^2/g$ or more and 7 $m^2/g$ or less, and still more preferably 3 $m^2/g$ or more and 7 $m^2/g$ or less.

When the specific surface area of the zinc oxide powder is in the above-described range, it is possible to improve the feeling of a cosmetic containing the zinc oxide powder. In the present invention, the content of the water-soluble substance in the zinc oxide powder refers to a value measured using the following method. Meanwhile, this measurement method is a measurement method according to "67. Water-Soluble Test Method" described in Japanese Standards of Quasi-drug Ingredients 2006 (JSQI).

The outline of this measurement method will be described below.

The zinc oxide powder (5 g) is weighed. Pure water (70 mL) is added to this zinc oxide powder, and the obtained liquid mixture is boiled for five minutes. Next, the liquid mixture is cooled, then, pure water is added to this liquid mixture so as to obtain a total amount of 100 mL, and furthermore, the components are mixed together. After that, the liquid mixture is filtered. In the filtration, the first filtrate (10 mL) obtained from the initiation of the filtration is removed, and then the subsequent filtrate (40 mL) is sampled. This sampled filtrate is evaporated to dryness on a water bath and then dried at 105° C. for one hour. In addition, the mass of the dried residue obtained by the drying of the filtrate is measured. A value obtained by dividing the measured mass of the dried residue by the mass of the first-measured zinc oxide powder is multiplied 2.5 times, expressed as a percentage, and considered as the content of the water-soluble substance in the zinc oxide powder.

(Measurement of Respective Contents of Alkali Metal and Alkaline Earth Metal in Water-Soluble Substance)

A filtrate (40 mL) sampled in the same manner as in the method for measuring the content of the water-soluble substance is prepared. The contents (concentrations) of the alkali metal and the alkaline earth metal in the water-soluble substance are measured using this filtrate and an inductively coupled plasma mass spectrometer (ICP-MS) (model No. 7500 cs, manufactured by Agilent Technologies).

(Measurement of Content of Zinc Oxide in Zinc Oxide Powder)

The content of the zinc oxide in the zinc oxide powder of the present invention refers to a value measured using the following method. Meanwhile, this measurement method is a measurement method according to "Zinc Oxide Quantitation Method" described in Japanese Standards of Quasi-drug Ingredients 2006 (JSQI).

A zinc oxide powder to be measured is put into a muffle furnace and strongly heated at 500° C. until the amount becomes constant (a state in which the mass does not change is formed). After that, the heated zinc oxide powder is cooled to room temperature in a glass desiccator into which silica gel is put. The cooled zinc oxide powder (1.5 g) is accurately measured. Water (50 mL) and dilute hydrochloric acid (20 mL) are added to the weighed zinc oxide powder, and the mixture is heated, thereby forming a solution in which the zinc oxide powder is dissolved. In a case in which an unnecessary substance remains, three drops of nitric acid is added thereto, thereby completely dissolving the unnecessary substance. The obtained solution is cooled to room temperature, and water is added thereto so as to obtain a total amount of 250 mL. The solution (25 mL) is sampled, an acetic acid and ammonium acetate buffer solution (10 mL) having a pH adjusted to 5.0 is added to the sampled solution, and furthermore, diluted ammonia water is added thereto, thereby adjusting the pH of the solution to 5 to 5.5. After that, water is added to the solution having an adjusted pH so as to obtain a total amount of 250 mL, and a xylenol orange reagent (0.5 mL) is added thereto as an indicator. The solution to which the indicator is added is titrated using a disodium edetate solution (0.05 mol/L) until the solution becomes yellow. The disodium edetate solution (0.05 mol/L, 1 mL) corresponds to zinc oxide (4.069 mg). From this fact, it is possible to determine the content of the zinc oxide in the zinc oxide powder using the amount of the disodium edetate solution (0.05 mol/L) necessary for the titration.

(Measurement of Specific Surface Area of Zinc Oxide Powder)

In the present invention, the specific surface area of the zinc oxide powder refers to a value measured using, for example, a full automatic specific surface area measurement instrument (trade name: MacsorbHMModel-1201, manufactured by Mountech Co., Ltd.) and the BET method.

[Surface-Treated Zinc Oxide Powder]

For the zinc oxide powder of the present invention, at least some of the surface thereof may be treated with at least one of an inorganic component and an organic component. The zinc oxide powder which is surface-treated with at least one of an inorganic component and an organic component as described above is referred to as surface-treated zinc oxide powder. The surface-treated zinc oxide powder is capable of further suppressing the surface activity of zinc oxide and capable of improving the dispersibility in the dispersion medium.

The inorganic component and the organic component can be appropriately selected and used depending on the applications of the zinc oxide powder.

In a case in which the surface-treated zinc oxide powder is used for cosmetics, the inorganic component and/or the organic component being used for the treatment are not particularly limited. It is possible to use, for example, surface treatment agents that are generally used for cosmetics.

Examples of the inorganic component include silica, alumina, and the like. These inorganic components may be used singly or two or more inorganic components may be used in combination.

Examples of the organic component include at least one component selected from the group consisting of a silicone compound, an organopolysiloxane, a fatty acid, a fatty acid soap, a fatty acid ester, a polyolefin, an N-acylamino acid or a salt thereof, an N-acyl-N-alkylamino acid or a salt thereof, hydrogenated lecitin and a salt thereof, and an organic titanate compound. These organic components may be used singly or two or more organic components may be used in combination.

In addition, a surfactant maybe used as an example of the inorganic component or the organic component.

In a case in which the zinc oxide powder is surface-treated using at least one selected from the inorganic component and the organic component, it is possible to suppress the surface activity of zinc oxide or improve the dispersibility of the zinc oxide powder in dispersion media.

Examples of the silicone compound that is used in the surface treatment include silicone oil such as methyl hydrogen polysiloxane, dimethyl polysiloxane, and methyl phenyl polysiloxane; alkylsilane such as methyl trimethoxysilane, ethyl trimethoxysilane, hexyl trimethoxysilane, octyl trimethoxysilane, and octyl triethoxysilane; fluoroalkyl silane such as trifluoro methyl ethyl trimethoxysilane and heptadecafluorodecyl trimethoxysilane, methicone, dimethicone, hydrogen dimethicone, triethoxysilylethyl polydimethylsiloxyethyl dimethicone, triethoxysilylethyl polydimethylsiloxyethylhexyl dimethicone, (acrylate/tridecyl acrylate/triethoxysilylpropyl methacrylate/dimethicone methacrylate) copolymers, triethoxycaprylylsilane, and the like.

These silicone compounds maybe used singly or two or more silicone compounds may be used in combination.

In addition, as the silicone compound, copolymers of these silicone compounds may also be used.

Among these silicone compounds, methicone, dimethicone, and hydrogen dimethicone are preferred, and hydrogen dimethicone are particularly preferred since these silicone compounds seldom impair the sebum solidification property of the zinc oxide powder.

Examples of the organic component will be further described.

Examples of the fatty acid include palmitic acid, isooctadecanoic acid, stearic acid, lauric acid, myristic acid, behenic acid, oleic acid, rosin acid, 12-hydroxystearic acid, polyhydroxystearic acid, and the like.

Examples of the fatty acid soap include aluminum stearate, calcium stearate, aluminum 12-hydroxystearate, and the like.

Examples of the fatty acid ester include dextrin fatty acid esters, cholesterol fatty acid esters, sucrose fatty acid esters, starch fatty acid esters, and the like.

Examples of the N-acylamino acid include N-lauroyl glutamic acid, N-myristoyl glutamic acid, N-palmitoyl glutamic acid, N-cocoyl glutamic acid, N-lauroyl lysine, N-stearoyl glutamic acid, lysine dilauroyl glutamate, and the like.

Examples of the salt of the N-acylamino acid include a sodium salt, a potassium salt, a magnesium salt, a calcium salt, an aluminum salt, a zinc salt, and the like of the N-acylamino acid.

In addition, instead of the N-acylamino acid and the salt thereof, Gemini-type amphiphilic amino acid including an N-acylamino acid salt such as sodium lysine dilauroyl glutamate may also be used.

Examples of the organic titanate compound include isopropyl triisostearoyl titanate, isopropyl dimethacryl isostearoyl titanate, isopropyl tri(dodecyl) benzene sulfonyl titanate, neopentyl (diallyl)oxy tri (dioctyl) phosphate titanate, neopentyl (diallyl)oxy trineodododecanoyl titanate, and the like.

In a case in which the surface-treated zinc oxide powder of the present invention is used for industrial applications of ultraviolet-shielding films or gas barrier films, in addition to or instead of the inorganic component or the organic component used for cosmetics, an ordinary dispersant being used to disperse particles can be appropriately selected and used. Examples of the dispersant include an anionic dispersant, a cationic dispersant, a nonionic dispersant, a silane coupling agent, a wetting dispersant, and the like.

In a case in which a surface treatment using the above-described dispersant is carried out, it is possible to suppress the surface activity of the zinc oxide powder or improve the dispersibility of the zinc oxide powder in dispersion media.

The method for manufacturing the surface-treated zinc oxide powder is not particularly limited, and well-known methods may be appropriately carried out depending on the components used in the surface treatment.

[Method for Manufacturing Zinc Oxide Powder]

A method for manufacturing the zinc oxide powder of the present invention is not particularly limited as long as the content of the water-soluble substance and the alkali metal and the alkaline earth metal can be controlled in desired ranges. For example, a raw material for producing the zinc oxide powder, for example, zinc oxalate, zinc hydroxide, zinc carbonate, basic zinc carbonate, or the like is prepared and cleaned so that the content of the water-soluble substance reaches 0.30% by mass or less. In a case in which the alkali metal and the alkaline earth metal are not in the above-described ranges, the zinc oxide powder may be produced using a raw material to which a salt of the alkaline earth metal is added.

Generally, in the zinc oxide powder, the alkali metal is more included than the alkaline earth metal as an impurity. However, an increase in the amount of the impurity in the zinc oxide powder is not preferable. Therefore, in the manufacturing of the zinc oxide powder, it is preferable to mix the salt of the alkaline earth metal to the minimum necessary extent.

In addition, the mass ratio between the alkali metal and the alkaline earth metal may be controlled by mixing the salt of the alkaline earth metal into the zinc oxide powder.

As described above, a desired zinc oxide powder can be obtained by combining cleaning or the addition of the salt of the alkaline earth metal as necessary.

The salt of the alkaline earth metal is not particularly limited as long as the time necessary for sebum to solidify can be shortened. The salt of the alkaline earth metal can be arbitrarily selected, and examples thereof include magnesium salts such as magnesium carbonate, magnesium oxide, magnesium hydroxide, magnesium chloride, magnesium sulfate, and magnesium acetate, calcium salts such as calcium carbonate, calcium oxide, calcium hydroxide, calcium chloride, calcium sulfate, and calcium acetate, strontium salts such as strontium carbonate, strontium oxide, strontium hydroxide, strontium chloride, strontium sulfate, and strontium acetate, barium salts such as barium carbonate, barium oxide, barium hydroxide, barium chloride, barium sulfate, and barium acetate, and the like. These salts of the alkaline earth metal may be used singly or two or more salts of the alkaline earth metal may be used in combination.

[Dispersion]

A dispersion of the present invention contains the zinc oxide powder of the present invention and a dispersion medium. The zinc oxide powder may be the surface-treated zinc oxide powder. The dispersion is capable of shortening the time necessary for the solidification of sebum.

Meanwhile, the dispersion of the present invention maybe a paste-form dispersion element having a high viscosity.

The content of the zinc oxide powder in the dispersion may be appropriately adjusted depending on desired characteristics.

In a case in which the dispersion is used for cosmetics, the content of the zinc oxide powder in the dispersion can be arbitrarily selected. For example, the content is preferably 30% by mass or more and 90% by mass or less, more preferably 40% by mass or more and 85% by mass or less, and still more preferably 50% by mass or more and 80% by mass or less.

When the content of the zinc oxide powder in the dispersion is limited, for example, set to a range of 30% by mass or more and 90% by mass or less, the dispersion is capable of containing a high concentration of the zinc oxide powder. Therefore, it is possible to improve the degree of freedom in formulations and set the viscosity of the dispersion at which handling is easy. Meanwhile, the content of the zinc oxide powder is not limited to the above-described range, and examples of the lower limit preferably include 10% by mass, 20% by mass, 40% by mass, 60% by mass, and the like. Examples of the upper limit preferably include 95% by mass, 90% by mass, 85% by mass, 75% by mass, and the like.

The viscosity of the dispersion of the present invention can be arbitrarily selected. For example, the viscosity is preferably 5 Pa·s or more and 300 Pa·s or less, more preferably 8 Pa·s or more and 100 Pa·s or less, still more preferably 10 Pa·s or more and 80 Pa·s or less, and most preferably 15 Pa·s or more and 60 Pa·s or less.

When the viscosity of the dispersion is within the above-described range, it is possible to obtain dispersions that can be easily handled even when, for example, including a high concentration of the solid content (zinc oxide powder).

The dispersion medium included in the dispersion is appropriately selected depending on the application of the dispersion. Examples of preferred dispersion media will be described below, but the dispersion medium in the dispersion is not limited thereto.

As the dispersion medium, for example, water, alcohols such as methanol, ethanol, 1-propanol, 2-propanol, 1-butanol, 2-butanol, octanol, and glycerin; esters such as ethyl acetate, butyl acetate, ethyl lactate, propylene glycol monomethyl ether acetate, and γ-butyrolactone; and ether such as diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, and diethylene glycol monoethyl ether can be used.

These dispersion media may be used singly or a mixture of two or more dispersion media may be used.

In addition, as other dispersion media, ketones such as acetone, methyl ethyl ketone, methyl isobutyl ketone, acetyl acetone, and cyclohexanone; aromatic hydrocarbons such as benzene, toluene, xylene, and ethyl benzene; cyclic hydrocarbon such as cyclohexane; amides such as dimethylformamide, N,N-dimethylacetoacetamide, and N-methylpyrrolidone; chain-like polysiloxanes such as dimethyl polysiloxane, methyl phenyl polysiloxane, and diphenyl polysiloxane; and the like can be used.

These dispersion media may be used singly or a mixture of two or more dispersion media may be used.

In addition, as an additional dispersion medium, cyclic polysiloxanes such as octamethyl cyclotetrasiloxane, decamethyl cyclopentasiloxane, and dodecamethyl cyclohexasiloxane; and denatured polysiloxanes such as amino-denatured polysiloxane, polyether-denatured polysilocane, alkyl-denatured polysiloxane, fluorine-denatured polysiloxane, and the like can be used.

These dispersion media may be used singly or a mixture of two or more dispersion media may be used.

In addition, as dispersion media other than the above-described dispersion media, hydrophobic dispersion media such as hydrocarbon oils such as liquid paraffin, squalene, isoparaffin, branched chain-like light paraffin, petrolatum, and ceresin, ester oils such as isopropyl myristate, cetyl isooctanoate, and glyceryl trioctanoate, silicone oils such as decamethyl cyclopentasiloxane, dimethyl polysiloxane, and methyl phenyl polysiloxane, higher fatty acids such as lauric acid, myristic acid, palmitic acid, and stearic acid, and higher alcohols such as lauryl alcohol, cetyl alcohol, stearyl alcohol, hexyl dodecanol, and isostearyl alcohol may also be used.

These dispersion media may be used singly or a mixture of two or more dispersion media may be used.

The above-described dispersion media can be used in arbitrary combination depending on characteristics being demanded. The amount of the dispersion medium can be arbitrarily selected and is, for example, generally 5% by mass to 90% by mass, preferably 10% by mass to 70% by mass, and more preferably 15% by mass to 60% by mass with respect to the total amount of the dispersion.

The dispersion of the present invention may include ordinarily-used additives as long as the characteristics thereof are not impaired.

Examples of the additives include dispersants, stabilizers, water-soluble binders, viscosity improvers, oil-soluble preservatives, ultraviolent absorbers, oil-soluble chemicals, oil-soluble pigments, oil-soluble proteins, plant oils, animal oils, and the like. The amount of each of the additives can be arbitrarily selected and is, for example, generally 0.1% by mass to 80% by mass, preferably 0.5% by mass to 50% by mass, and more preferably 1% by mass to 40% by mass with respect to the total amount of the dispersion.

The method for manufacturing the dispersion of the present invention is not particularly limited. Examples thereof include a method in which the zinc oxide powder and a dispersion medium are mechanically dispersed using a well-known dispersion apparatus.

Examples of a dispersion apparatus include a stirrer, a planetary mixer, a homogenizer, an ultrasonic homogenizer, a sand mill, a ball mill, a roll mill, and the like.

The dispersion of the present invention can be used for compositions and the like having an ultraviolet-shielding function, a gas transmission-suppressing function, and the like in addition to a cosmetic.

[Cosmetic]

A cosmetic of the present invention includes the zinc oxide powder of the present invention and/or the dispersion of the present invention and a cosmetic base raw material. The cosmetic is capable of suppressing make-up fading.

Here, the cosmetic base raw materials refer to various raw materials that form the main body of cosmetic products and can be arbitrarily selected. Examples thereof include oily raw materials, aqueous raw materials, surfactants, powder raw materials, and the like. These raw materials can be used in combination depending on necessity.

Examples of the oily raw material include oils and fats, higher aliphatic acids, higher alcohols, ester oils, and the like.

Examples of the aqueous raw materials include purified water, alcohols, viscosity improvers, and the like.

Examples of the powder raw material include colored pigments, white pigments, pearl agents, extender pigments, and the like.

The cosmetic of the present invention can be obtained by, for example, blending the zinc oxide powder or dispersion of the present invention into the cosmetic base raw materials such as emulsions, cream, foundation, lip sticks, blushes, or eye shadows using a well-known method.

In addition, the cosmetic can be obtained by blending the zinc oxide powder of the present invention into oil phases or water phases so as to produce O/W-type or W/O-type emulsions and then blending the emulsions with the cosmetic base raw materials.

The content of the zinc oxide powder in the cosmetic of the present invention may be appropriately adjusted depending on desired characteristics. For example, the lower limit of the content of the zinc oxide powder may be 0.01% by mass or more, 0.1% by mass or more, or 1% by mass or more. In addition, the upper limit of the content of the zinc oxide powder may be 50% by mass or less, 40% by mass or less, or 30% by mass or less. The content may be 20% by mass or less, 10% by mass or less, or 5% by mass or less.

EXAMPLES

Preferred examples of the present invention will be more specifically described using examples and comparative examples, but the present invention is not limited to the following examples.

Example 1

A zinc oxide powder (A1) (a water-soluble substance: 0.20% by mass, a content of an alkali metal: 12.5 µg/mL, a content of an alkaline earth metal: 11.5 µg/mL, the alkali metal:the alkaline earth metal (mass ratio)=1.1:1.0, a content of zinc oxide: 99.5% by mass, a specific surface area: 37 m$^2$/g) was prepared and used as a zinc oxide powder of Example 1.

Example 2

A zinc oxide powder (A2) (a water-soluble substance: 0.28% by mass, a content of an alkali metal: 29.2 µg/mL, a content of an alkaline earth metal: 3.1 µg/mL, the alkali metal:the alkaline earth metal (mass ratio)=9.4:1.0, a content of zinc oxide: 99.2% by mass, a specific surface area: 40 m$^2$/g) was prepared and used as a zinc oxide powder of Example 2.

Example 3

A zinc oxide powder (A3) (a water-soluble substance: 0.24% by mass, a content of an alkali metal: 20.5 µg/mL, a content of an alkaline earth metal: 4.4 µg/mL, the alkali metal:the alkaline earth metal (mass ratio)=4.7:1.0, a content of zinc oxide: 99.4% by mass, a specific surface area: 38 m$^2$/g) was prepared and used as a zinc oxide powder of Example 3.

Example 4

The zinc oxide powder (A1) of Example 1 (30 parts by mass), hydrogen dimethicone (1 part by mass), and isopropyl alcohol (69 parts by mass) were stirred and mixed together. Next, the isopropyl alcohol was removed, and the mixture was heated at 180° C. for 15 hours, thereby obtaining a surface-treated zinc oxide powder of Example 4.

Example 5

The zinc oxide powder (A1) of Example 1 (88.9 parts by mass) was injected into a Henschel mixer. While this zinc oxide powder (A1) was stirred and mixed, a liquid mixture of octyltriethoxysilane (trade name: KBE-3083, manufactured by Shin-Etsu Chemical Co., Ltd.) (4.4 parts by mass), pure water (0.4 parts by mass), and isopropyl alcohol (6.3 parts by mass) was added thereto, and the zinc oxide powder and the liquid mixture were mixed in the Henschel mixer and stirred for one hour.

Next, the obtained mixture was pulverized using a jet mill, and this pulverized powder was dried at 100° C., thereby obtaining a surface-treated zinc oxide powder of Example 5.

Comparative Example 1

A zinc oxide powder (A4) (a water-soluble substance: 0.05% by mass, a content of an alkali metal: 3.3 µg/mL, a content of an alkaline earth metal: 0.21 µg/mL, the alkali metal:the alkaline earth metal (mass ratio) =15.7:1.0, a content of zinc oxide: 99.9% by mass, a specific surface area: 29 m$^2$/g) was prepared and used as a zinc oxide powder of Comparative Example 1. In this sample, the amount of the water-soluble substance was in the range of the present invention, but the amount of the alkaline earth metal with respect to the amount of the alkali metal was small.

Comparative Example 2

A zinc oxide powder (A5) (a water-soluble substance: 0.94% by mass, a content of an alkali metal: 88.8 µg/mL, a content of an alkaline earth metal: 13.3 μg/mL, the alkali metal:the alkaline earth metal (mass ratio)=6.7:1.0, a content of zinc oxide: 98.0% by mass, a specific surface area: 24 m²/g) was prepared and used as a zinc oxide powder of Comparative Example 2. In this sample, the mass ratio between the alkali metal and the alkaline earth metal was in the range of the present invention, but the amount of the water-soluble substance was outside the range of the present invention.

[Evaluation of Sebum Solidification Property]

"Production of Artificial Sebum"

Oleic acid (manufactured by Kanto Kagaku) (10 g), squalene (10 g) (manufactured by Kanto Kagaku), olive oil (10 g) (trade name: EX VIRGIN OIL, manufactured by BOSCO Co., Ltd.) were mixed together, thereby producing artificial sebum.

Each of the zinc oxide powders of Examples 1 to 5 and Comparative Examples 1 and 2 (1 g) and the artificial sebum (4 g) were mixed together and stirred using a stirrer, the time taken for the artificial sebum to solidify in a stirred state was measured, and the sebum solidification property was evaluated.

As a result, the zinc oxide powder of Example 1 solidified in two minutes, the zinc oxide powder of Example 2 solidified in nine minutes, the zinc oxide powder of Example 3 solidified in seven minutes, the surface-treated zinc oxide powder of Example 4 solidified in one minute, and the surface-treated zinc oxide powder of Example 5 solidified in 5.5 minutes. In addition, the zinc oxide powder of Comparative Example 1 did not solidify even in 60 minutes, and the zinc oxide powder of Comparative Example 2 solidified in 60 minutes. The results are shown in Table 1.

Example 5, and the surface-treated zinc oxide powder of Comparative Example 1. The results are shown in Table 2.

TABLE 2

|  | Example 1 | Example 4 | Example 5 | Comparative Example 1 |
| --- | --- | --- | --- | --- |
| Oleic acid | 0.25 minutes | 0.75 minutes | 6 minutes | 120 minutes |
| Squalene | >1440 minutes | >1440 minutes | >1440 minutes | >1440 minutes |
| Olive oil | >1440 minutes | >1440 minutes | >1440 minutes | >1440 minutes |
| Cyclopentasiloxane | >1440 minutes | >1440 minutes | >1440 minutes | >1440 minutes |
| Caprylic/capric triglyceride | >1440 minutes | >1440 minutes | >1440 minutes | >1440 minutes |

The evaluation of the selectivity of the oil showed that, in the zinc oxide powder of Example 1, the surface-treated zinc oxide powder of Example 4, and the surface-treated zinc oxide powder of Example 5, the oleic acid solidified, but other oils did not solidify. Therefore, it was confirmed that the zinc oxide powders of Examples 1, 4, and 5 had a selectivity of oil regarding the solidification.

In addition, it was confirmed that the zinc oxide powders of Examples 4 and 5 had a sebum solidification property even when surface-treated. In addition, from the evaluation results of the selectivity of oil regarding the zinc oxide powder of Example 1 and the surface-treated zinc oxide powder of Example 4, it was confirmed that, in a case in which the zinc oxide powder was surface-treated with

TABLE 1

|  | Example 1 | Example 2 | Example 3 | Example 4 | Example 5 | Comparative Example 1 | Comparative Example 2 |
| --- | --- | --- | --- | --- | --- | --- | --- |
| Content of water-soluble substance (% by mass) | 0.20 | 0.28 | 0.24 | 0.20 | 0.20 | 0.05 | 0.94 |
| Content of alkali metal (μg/mL) | 12.5 | 29.2 | 20.5 | 12.5 | 12.5 | 3.3 | 88.8 |
| Content of alkaline earth metal (μg/mL) | 11.5 | 3.1 | 4.4 | 11.5 | 11.5 | 0.21 | 13.3 |
| Alkali metal:alkaline earth metal (mass ratio) | 1.1:1.0 | 9.4:1.0 | 4.7:1.0 | 1.1:1.0 | 1.1:1.0 | 15.7:1.0 | 6.7:1.0 |
| Content of zinc oxide (% by mass) | 99.5 | 99.2 | 99.4 | 99.5 | 99.5 | 99.9 | 98.0 |
| Specific surface area (m²/g) | 37 | 40 | 38 | 37 | 37 | 29 | 24 |
| Solidification time of artificial sebum (minutes) | 2 | 9 | 7 | 1 | 5.5 | >60 | 60 |

From the above-described evaluation of the sebum solidification property, it was confirmed that the zinc oxide powder in which the content of the water-soluble substance was 0.30% by mass or less, and the mass ratio between the alkali metal and the alkaline earth metal which were included in the water-soluble substance was adjusted to 1:2 to 10:1 shortened the time during which the sebum could solidify. As a result, it is considered that make-up fading can be suppressed.

"Evaluation of Selectivity"

The components were mixed and stirred in the same manner as in the evaluation of the sebum solidification property except for the fact that, instead of the artificial sebum, oleic acid, squalene, olive oil, cyclopentasiloxane, and caprylic/capric triglyceride were used, and the selectivity was evaluated. Specifically, the selectivity of oil that solidified the powder was evaluated using the zinc oxide powder of Example 1, the surface-treated zinc oxide powder of Example 4, the surface-treated zinc oxide powder of hydrogen dimethicone, the hydrogen dimethicone rarely impaired the sebum solidification property of the zinc oxide powder.

INDUSTRIAL APPLICABILITY

The zinc oxide powder of the present invention is excellent in terms of the sebum solidification property and thus has a great industrial value when used for cosmetics.

The invention claimed is:

1. A cosmetic zinc oxide powder comprising,
   a zinc oxide having an untreated surface,
   a water-soluble substance derived from impurity of the zinc oxide powder, wherein the water-soluble substance comprises an alkali metal and an alkaline earth metal, and wherein the water-soluble substance is at 0.010% by mass or more and 0.30% by mass or less as defined by the Water-Soluble Test Method described in Japanese Standards of Quasi-drug Ingredients 2006, a mass ratio between the alkali metal and the alkaline earth metal in a range of 1:2 to 10:1, wherein the alkaline earth metal included in the water-soluble substance is 0.0001% by mass to 0.2% by mass with respect to the total amount of the zinc oxide powder, wherein, the mass ratio between an alkali metal and an alkaline earth metal is obtained from respective concentrations of the alkali metal and the alkaline earth metal in the water-soluble substance, wherein the concentrations are measured as defined by the Water-Soluble Test Method described in Japanese Standards of Quasi-drug Ingredients 2006.

2. The cosmetic zinc oxide powder according to claim 1, wherein a content of zinc oxide is 99.0% by mass or more.

3. The cosmetic zinc oxide powder according to claim 1, wherein a specific surface area of the zinc oxide powder is 8 m$^2$/g or more and 65 m$^2$/g or less.

4. A cosmetic zinc oxide powder comprising,
a zinc oxide, wherein the zinc oxide is surface-treated with at least one of an inorganic component and an organic component,
a water-soluble substance derived from impurity of the zinc oxide powder, wherein the water-soluble substance comprises an alkali metal and an alkaline earth metal, and wherein the water-soluble substance is at 0.010% by mass or more and 0.30% by mass or less as defined by the Water-Soluble Test Method described in Japanese Standards of Quasi-drug Ingredients 2006,
a mass ratio between the alkali metal and the alkaline earth metal in a range of 1:2 to 10:1, wherein the alkaline earth metal included in the water-soluble substance is 0.0001% by mass to 0.2% by mass with respect to the total amount of the zinc oxide powder,
wherein, the mass ratio between an alkali metal and an alkaline earth metal is obtained from respective concentrations of the alkali metal and the alkaline earth metal in the water-soluble substance, wherein the concentrations are measured as defined by the Water-Soluble Test Method described in Japanese Standards of Quasi-drug Ingredients 2006.

5. The cosmetic zinc oxide powder according to claim 4, wherein the inorganic component is at least one selected from silica and alumina, and
the organic component is at least one selected from the group consisting of a silicone compound, organopolysiloxane, a fatty acid, fatty acid soap, a fatty acid ester, a polyolefin, N-acylamino acid or a salt thereof, N-acyl-N-alkylamino acid or a salt thereof, hydrogenated lecitin or a salt thereof, and an organic titanate compound.

6. A dispersion comprising:
the cosmetic zinc oxide powder according to claim 1; and
a dispersion medium.

7. A cosmetic comprising:
the cosmetic zinc oxide powder according to claim 1; and
a cosmetic base raw material.

8. The cosmetic according to claim 7, wherein the cosmetic comprises a dispersion medium.

9. The cosmetic zinc oxide powder according to claim 1, wherein the content of the alkaline earth metal included in the water-soluble substance is 0.001% by mass to 0.2% by mass with respect to the total amount of the zinc oxide powder.

10. A cosmetic zinc oxide powder comprising
a zinc oxide having an untreated surface and
a water-soluble substance derived from impurity of the zinc oxide powder, wherein the water-soluble substance comprises an alkali metal and an alkaline earth metal,
wherein a content of the zinc oxide is 99.0% by mass or more,
a content of the water-soluble substance is 0.010% by mass or more and 0.30% by mass or less,
a mass ratio between the alkali metal and the alkaline earth metal is in a range of 1:2 to 10:1,
a specific surface area of the zinc oxide powder is 8 m$^2$/g or more and 65 m$^2$/g or less, the content of a water-soluble substance in the zinc oxide powder is expressed as a percentage and is determined using a measurement method according to the Water-Soluble Test Method described in Japanese Standards of Quasi-drug Ingredients 2006.

11. The cosmetic zinc oxide powder according to claim 10, wherein the specific surface area of the zinc oxide powder is 15 m$^2$/g or more and 60 m$^2$/g or less.

12. The cosmetic zinc oxide powder according to claim 10, wherein the specific surface area of the zinc oxide powder is 20 m$^2$/g or more and 50 m$^2$/g or less.

13. The cosmetic zinc oxide powder according to claim 10, wherein a content of the alkaline earth metal included in the water-soluble substance is 0.001% by mass to 0.2% by mass with respect to the total amount of the zinc oxide powder.

14. The cosmetic zinc oxide powder according to claim 1, wherein the zinc oxide powder when use causes solidification of sebum in one hour or less.

15. The cosmetic zinc oxide powder according to claim 1, wherein the zinc oxide powder when use is capable of selectively solidifying oleic acid in a sebum.

16. The cosmetic zinc oxide powder according to claim 1, wherein the mass ratio between the alkali metal and the alkaline earth metal is in a range of 1.1:1.0 to 10:1.

17. The cosmetic zinc oxide powder according to claim 4, wherein the mass ratio between the alkali metal and the alkaline earth metal is in a range of 1.1:1.0 to 10:1.

18. The cosmetic zinc oxide powder according to claim 4, wherein the inorganic component is substantially free from silica.

19. A cosmetic comprising:
the cosmetic zinc oxide powder according to claim 4; and
a cosmetic base raw material.

20. The cosmetic according to claim 19, wherein the cosmetic comprises a dispersion medium.

* * * * *